(12) United States Patent
Koivunen et al.

(10) Patent No.: US 6,624,144 B1
(45) Date of Patent: Sep. 23, 2003

(54) MATRIX METALLOPROTEINASE INHIBITORS AND DOWN-REGULATORS

(75) Inventors: Erkki Koivunen, Hyvinkää (FI); Timo Sorsa, Helsinki (FI); Tuula Salo, Oulu (FI)

(73) Assignee: CTT Cancer Targeting Technologies Oy, Helsinki (FI)

( * ) Notice: Subject to any disclaimer, the term of this patent is extended or adjusted under 35 U.S.C. 154(b) by 0 days.

(21) Appl. No.: 09/646,423

(22) PCT Filed: Mar. 17, 1999

(86) PCT No.: PCT/FI99/00204

§ 371 (c)(1),
(2), (4) Date: Nov. 20, 2000

(87) PCT Pub. No.: WO99/47550

PCT Pub. Date: Sep. 23, 1999

(30) Foreign Application Priority Data

Mar. 18, 1998 (FI) .................................................. 980604

(51) Int. Cl.⁷ ............................ C07K 7/06; A61K 38/08
(52) U.S. Cl. ................................ 514/9; 514/11; 514/15; 530/317; 530/328; 530/334; 530/344; 530/354; 530/360; 435/219
(58) Field of Search ................................ 514/9, 11, 15; 530/317, 328, 334, 360, 354, 344; 435/219

(56) References Cited

U.S. PATENT DOCUMENTS 4,666,897 A  5/1987  Golub et al.
5,652,227 A  7/1997  Teronen et al.

FOREIGN PATENT DOCUMENTS

WO   WO-9611209   4/1996

OTHER PUBLICATIONS

R. P. Beckett et al., DDT, vol. 1, No. 1, pp. 16–24, Jan. 1996.
H. Birkedal–Hansen, Current Opinion in Cell Biology 1995, 7:728–735.
B. L. Roberts et al. Proc. Natl. Acad. Sci. USA, vol. 89, pp. 2429–2433 (Mar. 1992).
W. G. Stetler–Stevenson et al., Annu. Rev. Cell Biol. 1993, 9:541–73.
O. V. Volpert et al., J. Clin. Invest., vol. 98, No. 3, 671–679 (Aug. 1996).

*Primary Examiner*—Christopher S. F. Low
*Assistant Examiner*—Chih-Min Kam
(74) *Attorney, Agent, or Firm*—Birch, Stewart, Kolasch & Birch, LLP

(57) ABSTRACT

The present invention relates to novel matrix metalloproteinase (MMP) inhibitors and down-regulators, to a process for the preparation of these inhibitors, to pharmaceutical compositions comprising these inhibitors/down-regulators, to the use of the novel MMP inhibitors for the manufacture of pharmaceutical and research preparations, to a method for inhibiting and down-regulating MMP-dependent conditions either in vivo or in vitro, to a method for inhibiting formation, synthesis, expression activations, and/or functions as well as actions of matrix metalloproteinases, and to the use of the novel MMP inhibitors and down-regulators in biochemical isolation and purification procedures of matrix metalloproteinases.

6 Claims, 9 Drawing Sheets

MB-435 breast carcinoma cells grown for 2 days in 10 % serum

CTTHWGFTLC

200 µg/ml

500 µg/ml

|  | relative amount of MMP/<br>relative cell number |
|---|---|
| 1. Control | 1.0 |
| 2. TGFβ 1 ng/ml | 2.8 |
| 3. TGFβ 10 ng/ml | 3.7 |
| 4. TGFβ 20 ng/ml | 3.9 |
| 5. P291 50 μg/ml | 1.7 |
| 6. P291 100 μg/ml | 1.4 |
| 7. P291 250 μg/ml | 0.6 |
| 8. P291 500 μg/ml | 0.6 |
| 9. P291 50 μg/ml and TGFβ 10 ng/ml | 2.2 |
| 10. P291 100 μg/ml and TGFβ 10 ng/ml | 0.7 |
| 11. P291 250 μg/ml and TGFβ 10 ng/ml | 0.3 |
| 12. P291 500 μg/ml and TGFβ 10 ng/ml | 0.2 |

(P291 = CTTHWGFTLC)

|  |  | Calculated areas (5) of migrated cells |
|---|---|---|
| C | control cells | 100 % |
| T10 | TGFβ 10 ng/ml | 139 % |
| P50 | P291 50 μg/ml | 60 % |
| P250 | P291 250 μg/ml | 69 % |
| P500 | P291 500 μg/ml | 69 % |
| T+P250 | TGFβ 10 ng/ml and P291 250 μg/ml | 76 % |
| T+P500 | TGFβ 10 ng/ml and P291 500 μg/ml | 65 % |

(P291 = CTTHWGFTLC)

MATRIX METALLOPROTEINASE INHIBITORS AND DOWN-REGULATORS

This application is the national phase under 35 U.S.C. §371 of PCT International Application No. PCT/FI99/00204 which has an International filing date of Mar. 17, 1999, which designated the United States of America.

A The present invention relates to novel matrix metalloproteinase (MMP) inhibitors and down-regulators, to a process for the preparation of these inhibitors, to pharmaceutical compositions comprising these inhibitors/downregulators, to the use of the novel matrix metalloproteinase inhibitors for the manufacture of pharmaceutical and research preparations, to a method for inhibiting and down-regulating MMP-dependent conditions either in vivo or in vitro, to a method for inhibiting formation, synthesis, expression and/or functions as well as actions of matrix metalloproteinases, and to the use of the novel MMP inhibitors in biochemical isolation and purification procedures of matrix metalloproteinases.

Matrix metalloproteinases (MMPs) constitute a superfamily of genetically closely related proteolytic enzymes capable of degrading almost all the constituents of extracellular matrix and basement membrane that restrict cell movement. MMPs also process serpins, cytokines and growth factors as well as certain cell surface components (Woessner, 1991; Birkendal-Hansen, 1995; Chandler et al., 1997). MMPs are thought to have a key role in mediating tissue remodeling and cell migration during morphogenesis and physiological situations such as wound healing, trophoblast implantation and endometrial menstrual breakdown. MMPs are further involved in processing and modification of molecular phenomena such as tissue remodeling, angiogenesis, cytokine, growth factor, inte grin and their receptor processing (Chandler et al., 1997). MMPs also mediate release and membrane-bound proteolytic processing of tumor necrosis factor (TNF-α) by bacterial-virulence factor induced monocytes. This event is mediated by a membrane-bound metalloproteinase TACE (TNF-α activating enzyme). Thus MMP-inhibitors, such as the novel peptides presented in this invention, can i.a. prevent activation of TNF-α by blocking this type of activating enzymes (Shapira et al., 1997).

Several studies have shown that the expression and activities of MMPs are pathologically elevated over the body's endogenous anti-proteinase shield in a variety of diseases such as cancer, metastatis, rheumatoid arthritis, multiple sclerosis, periodontitis, osteoporosis, osteosarcoma, osteomyelitis, bronchiectasis, chronic pulmonary obstructive disease, and skin and eye diseases. Proteolytic enzymes, especially MMPs, are believed to contribute to the tissue destruction damage associated with these diseases.

There is a variety of other disorders in which extracellular protein degradation/destruction plays a prominent role. Examples of such diseases include arthritides, acquired immune deficiency syndrome (AIDS), burns, wounds such as bed sores and varicose ulcers, fractures, trauma, gastric ulceration, skin diseases such as acne and psoriasis, lichenoid lesions, epidermolysis bollosa, aftae (reactive oral ulcer), dental diseases such as periodontal diseases, peri-implantitis, jaw and other cysts and root canal treatment or endodontic treatment, related diseases, external and intrinsic root resorption, caries etc.

At least 20 members of the MMP-superfamily are known (Birkendal-Hansen, 1995; Pei & Weiss, 1996; Llano et al., 1997), and the number of MMP-family members and their cellular origins is growing all the time. Each of the MMP enzymes contains a putative tridentate $Zn^{2+}$ binding site which is believed to constitute the active site in the enzyme. Very recently, three new members of the MMP-family were discovered by screening cDNA libraries for homologies to conserved regions of the known MMP genes and named the membrane-type matrix metalloproteinases-1, -2, and -3 (MT-MMP-1, -2, and-3). Based on their predicted amino acid sequences, each of the MT-MMPs like almost all previously characterized MMPs, contains (i) a candidate leader sequence, (ii) a propeptide region which includes a highly conserved PRCGXPD(SEQ ID NO:12) sequence that helps to stabilize the MMP zymogen in a catalytically inactive state, (iii) a zinc-binding catalytic domain, and (iv) a hemopexin-like domain near their respective C-termini. In addition, in a pattern similar to that described for stromelysin-3, each of the MT-MMPs contains a short amino acid insert sandwiched between their pro- and catalytic domains that encodes a potential recognition motif for members of the proprotein convertase family. Despite their considerable similarity to other MMP family members, however, only the MT-MMPs contain approximately 75–100 amino acid extensions at their C-termini, each of which includes a hydrophobic stretch consistent with the presence of a transmembrane (TM) domain. Thus, in contradistinction to all other MMPs, the MT-MMPs are expressed as membrane-associated ectoenzymes rather than soluble proteins (Pei & Weiss, 1996).

A comprehensive review of the MMP-family members, their activation, modes of action, their inhibition by various natural proteins (endogenous inhibitors) and synthetic compounds as well as details of the involvement of MMP family members in various pathological conditions and diseases is given by Woessner (1991); Krane (1994); Birkendal-Hansen et al. (1993); and Birkendal-Hansen (1995), the whole disclosures of which are incorporated herein by reference. In the scope of the present invention the term matrix metalloproteinase (MMP) refers to all discovered MMPs.

The gelatinase A or 72 kDa MMP-2 and gelatinase B or 92 kDa MMP-9 were originally described as type IV collagenases because they appeared to be essential enzymes for the degradation of the basement membrane (Tryggvason et al., 1987). Cells need to traverse the endothelial basement membrane during entry to and exit from the circulation. This is also a critical key step in the metastatic cascade tumor cells have to accomplish before they can metastasize to distant organs. MMP-2 and MMP-9 may also have a function in other steps of the metastatic cascade such as in angiogenesis (Hanahan & Folkman, 1996; Volpert et al., 1996) and local tumor invasion (Stetler-Stevenson et al., 1993).

Because MMPs are potential targets for therapeutic intervention, much work has been focused on the design of synthetic metalloproteinase inhibitors. Many MMP-inhibiting compounds containing reactive zinc-chelating groups such as thiol, hydroxamate, EDTA, phosphonamidate, phosphinate etc. have been developed (Beckett et al., 1996). Some of the peptidomimetics have shown beneficial effects in animal models of metastasis, arthritis, and other inflammatory diseases. Tumor cell invasion can also be inhibited by the native MMP inhibitors TIMP-1 (tissue inhibitor of metalloproteinase) and TIMP-2. MMPs can also be inhibited by peptides based on the highly conserved prodomain region of MMPs that is important for latency of MMPs (Park et al., 1991; Melchiori et al., 1992; Fotouhi et al., 1994). In addition, tetracyclines and their nonantimicrobial chemically-modified (CMT) as well as anthracycline derivatives have been found to inhibit MMPs (Golub et al., 1992; Sorsa et al., 1994).

Although the above discussion shows that some inhibitors for MMPs do exist and have been investigated, the tests are still mostly at the experimentation stage and no clinically acceptable inhibitor for MMPs exists as a therapeutic or prophylactic drug for any of the pathological states and diseases potentially connected with MMPs. Adverse side effects which have been detected in the above described MMP inhibitors include, for instance, toxicities (synthetic peptides), antimicrobial activities (tetracyclines), etc.

An alternative to rational molecular design is to screen libraries of random peptides or other chemicals to find lead compounds binding to target molecules. In particular, peptide libraries displayed on the surface of bacteriophage have often yielded valuable binding peptides to target proteins. However, it has been more difficult to isolate inhibitors to proteinases from libraries of short peptides, possibly because short peptides are easily degraded by proteinases. Phage-displayed peptide libraries have rather been utilized to obtain information of the sequences cleaved by a proteinase (Matthews & Wells, 1993; Smith et al., 1995). Inhibitors to proteinases have been developed with phage surface expression and selection of large proteinase inhibitor domains in which certain active site residues have been randomized (Roberts et al., 1992; Dennis et al., 1995).

The present inventors have now succesfully isolated novel peptide inhibitors to MMPs, especially to MMP-9 and MMP2, using phage-displayed libraries of peptides that were conformationally restrained by designed disulfide bonds. The most active MMP inhibitors developed are capable of inhibiting in vitro migration of endothelial cells as well as invasion of tumor cells, thus being potential lead compounds to design peptidomimetics to block MMPs. The peptides can also be used in column chromatographic matrices for biochemical isolation and purification procedures of MMPS.

It is therefore an object of the present invention to provide novel matrix metalloproteinase inhibitors and binding-ligands based on the cyclic structure (disulfide bond between cysteines) of the peptide motif

CXXHWGFXXC which corresponds to the sequence shown in SEQ ID No. 1 of the sequence listing and wherein X is any amino acid residue.

It is another object of the present invention to provide novel matrix metalloproteinase inhibitors and down-regulators based on the cyclic structure of the peptide motifs

CRRHWGFEFC which corresponds to the sequence shown in SEQ ID No. 2, and

CTTHWGFTLC which corresponds to the sequence shown in SEQ ID No. 3.

The present invention also relates to a pharmaceutical composition comprising an amount of the novel matrix metalloproteinase inhibitor(s)/down-regulator(s) effective to reduce the activities, activations, functions, and/or expressions of one or more MMPs, especially of MMP-2 and/or MMP-9, and a pharmaceutically and biochemically acceptable carrier. Pharmaceutical compositions comprising novel MMP inhibitor(s)/down-regulator(s) according to the invention may be used systemically, locally and/or topically. They also include all potential combinations (combo-medications) with other MMP-inhibitors, other drugs and tumor-homing chemicals/molecules.

The present invention also includes the use of the novel matrix metalloproteinase inhibitors for the manufacture of pharmaceutical preparations for the treatment of matrix metalloproteinase dependent conditions, and also their use, for example as affinity ligands, in biochemical purification and isolation procedures of MMPs. The MMP-dependent conditions include, but are not limited to, wounds, burns, fractures, lesions, ulcers, cancer and metastasis progression in connective tissues and bone, periodontitis, gingivitis, peri-implantitis, cysts, root canal treatment, internal and external root canal resorption, caries, AIDS, corneal ulceration, gastric ulceration, aftae, trauma, acne, psoriasis, loosening of the endosseal hip-prosthesis, osteomyelitis, osteoporosis, tissue remodeling, angiogenesis, arthritides (rheumatoid, reactive and osteo arthritides), angiogenesis, lung diseases (bronchiectasis and chronic obstructive pulmonary diseases and other lung diseases).

The present invention also relates to a process for the preparation of novel matrix metalloproteinases which process comprises standard solid-phase Merrifield peptide synthesis.

The novel CXXHWGFXXC(SEQ ID NO:1) structure according to the invention does not show similarity to previously described MMP inhibitors, although the activities of CTTHWGFTLC(SEQ ID NO:3) resemble the properties of chemically modified tetracyclines (CMTs) as will be described below. The peptides comprising the novel structure were derived from the single cysteine-expressing $CX_9$ library and exhibited a HWGF(SEQ ID NO:13) consensus sequence. All contained a second cysteine showing a cyclic structure CXXHWGFXXC(SEQ ID NO:1). Phage attachment experiments indicated that the cloned phages bound to MMP-9 with considerable affinity.

The cyclic peptides according to the invention inhibited degradation of gelatin and casein substrates by MMP-2 and MMP-9 with $IC_{50}$ of 5–10 $\mu$g/ml. Of a series of peptides synthesized, the HWGF(SEQ ID NO:13)-containing peptides CRRHWGFEFC(SEQ ID NO:2) and CTTHWGFTLC (SEQ ID NO:3) were found to be most promising as inhibitors of MMP-9. These two HWGF(SEQ ID NO:13)-containing peptides also inhibited MMP-2. The fact that the peptides were selected on MMP-9 but can strongly inhibit also MMP-2 indicates that the peptides recognize a binding site very similar between MMP-9 and MMP-2.

The most active HWGF(SEQ ID NO:13)-containing peptide developed (CTTHWGFTLC)(SEQ ID NO:3) inhibited cell migration studied in normal serum-containing media, and blocked the migration of human endothelial cells as well as invasion of HT1080 fibrosarcoma and C8161 melanoma cells through a reconstituted basement membrane. These findings imply that both cancer cells and endothelial cells may use quite a similar MMP-dependent mechanism to migrate that is sensitive to the down-regulating effect of CTTHWGFTLC(SEQ ID NO:3). The high activity of CTTHWGFTLC(SEQ ID NO:3) could at least partially be due to the fact that the peptide can not only inhibit an active enzyme but can interfere with the autoactivation of purified proMMP-9 and proMMP-2 as is shown below by using gelatin and casein substrates. The peptide can also down-regulate the production of MMP-9. In contrast to the phage binding data in which we were unable to see any phage binding to proMMP-9, the synthetic CTTHWGFTLC(SEQ ID NO:3) peptide does bind to proMMP-9 as indicated by single-step isolation of proMMP-9 from human leukocyte buffy coats using affinity chromatography with the peptide coupled to Sepharose. On the whole, it is possible that by binding to proMMPs the peptide can hinder the true proteolytic activation by other proteinases that is the likely activation mechanism during cell invasion.

The corresponding linear peptides were virtually inactive as demonstrated by a loss of activity after reduction and alkylation of the cysteines. Especially preferred MMP inhibitors according to the present invention are thus the cyclic peptide inhibitors CTTFIWGFTLC(SEQ ID NO:3) and CRRHWGFEFC(SEQ ID NO:2), which inhibit the activity of MMP-2 and MMP-9 as shown below.

As stated above, the novel cyclic peptide inhibitors we have developed are useful lead compounds to design peptidomimetics to block MMPs and cell migration. The CXXHWGFXXC(SEQ ID NO:1) motif may also be utilized to develop more selective inhibitors to individual members of the MMP family, as MMP-2 and MMP-9 were differently inhibited by the two CXXHWGFXXC(SEQ ID NO:1) peptides: MMP-2 was more strongly inhibited by CTTHWGFTLC(SEQ ID NO:3) while MMP-9 was preferentially inhibited by CRRHWGFEFC(SEQ ID NO:2). Selective inhibitors directed e.g. to MMP-2 might be more efficient in preventing tumor dissemination, as in many experimental systems the metastatic potential of tumor cells rather correlated with MMP-2 activity rather than with MMP-9 activity. Finally the small size of the MMP-targeting cyclic peptides can be utilized to carry drugs to tumors. Phage-library derived peptides targeting receptors in tumor vasculature have been found to be useful cytotoxic drug carriers to tumors in mice. MMPs are potential receptors for targeted chernotherapy, because they are usually overexpressed in tumors as compared to normal tissues and appear to be involved in the angiogenic process.

Thus, as a result of the invention, MMP dependent conditions may now be treated or prevented either with the novel MMP inhibitors alone or in combination with other drugs normally used in connection with the disease or disorder in question. These include for example tetracyclines, chemically modified tetracyclines (Golub et al., 1992), bisphosphonates, as well as homing/carrier molecules to the sites of tumors, such as integrin-binding peptides (Arap et al., 1998). The amount of novel matrix metalloproteinase inhibitors to be used in the pharmaceutical compositions according to the present invention varies depending on the specific inhibitor used, the patient and disease to be treated as well as the route of administration.

The novel MMP inhibitors of the present invention have shown no toxicity when injected into animals and do not affect cell number or viability as determined by trypan blue dye exclusion.

The present invention thus also relates to a method for the therapeutic or prophylactic treatment of MMP-dependent conditions in mammals by administering to said mammal an effective amount of the novel MMP-inhibitor(s), as well as to a method for inhibiting the formations, synthesis, expressions, activations, functions and actions of MMPs in mammals by administering the novel MMP-inhibitor(s)/down-regulator(s) in an amount which is effective in blocking the formation, activation and actions of MMPs.

The present invention also relates to a method for inhibiting matrix metalloproteinases in vitro comprising adding to an in vitro system the novel matrix metalloproteinase inhibitor(s) in an amount which is effective in inhibiting the MMP activity.

A further object of the invention is a method for isolating and purifying matrix metalloproteinases with the aid of the novel matrix metalloproteinase inhibitor(s).

FIG. 1 shows the results from the inhibition of MMP-9-mediated [$^{125}$I]-gelatin degradation using synthetic peptides. APMA-activated MMP-9 was preincubated with the CRRHWGFEFC(SEQ ID NO:2) and CTTFIWGFTLC(SEQ ID NO:3) at the concentrations indicated for 1 h before adding [$^{125}$I]-gelating substrate. After gelatinolysis for 1h, the counts released into medium were determined. The results show means from duplicate measurements. Similar results were obtained in three independent experiments.

FIG. 2 shows gelatinolysis induced by APMA-activated MMPs or their proforms. The concentrations of the cyclic and linear CRRHWGFEFC(SEQ ID NO:2) peptide were 10 µg/ml. The results show means from duplicate experiments.

FIG. 3 shows inhibition of MMP-2-mediated casein degradation by CTTHWGFTLC(SEQ ID NO:3) (A, B) and CRRHWGFEFC(SEQ ID NO:2) (C, D). After 1 h pretreatment with the peptides, APMA-activated MMP-2 (A, C) or proMMP-2 (B, D) was incubated with the casein for 2 h. 52 µM β-casein was used as substrate for MMPs. Shown is Coomassie Blue-staining of the 21 kD β-casein (lane 1) and its fragments (lanes 2–9) resolved by SDS-PAGE (A, B); CTTHWGFTLC(SEQ ID NO:3) was used at the concentrations of (2) 0 µg/ml, (3) 75, (4) 50, (5) 25, (6) 10, (7) 5, (8) 1, and (9) 0.5 µg/ml in the lanes 2–9, respectively. (C, D); the concentrations of CRRHWGFEFC(SEQ ID. NO:2) were 0, 250, 100, 50, 25, 10, 1, and 0.5 µg/ml, respectively.

FIG. 4 shows binding of proMMP-9 to CTTHWGFTLC (SEQ ID NO:3) peptide coupled to Sepharose. Lysate of human buffy coat cells was applied to each peptide Sepharose, and the bound proteins were analyzed on SDS gels followed by Coomassie Blue staining (lanes 1–2), or immunoblotting with anti-MMP-9 antibodies (lanes 5–6). Lanes 1 and 5 show proteins eluted from CTTHWGFTLC (SEQ ID NO:3)-Sepharose. Lanes 2 and 6 show proteins eluted from GACLRSGRGCGA(SEQ ID NO:5)-Sepharose. Lane 3 shows protein staining of the cell lysate. Lane 4 displays the molecular weight markers of 200, 92, 76, and 55 kDa.

FIG. 5 shows how CTTHWGFTLC(SEQ ID NO:3) inhibits migration of HT1080 fibrosarcoma cells. Cells were pretreated with CTTHWGFTLC(SEQ ID NO:3) at the concentrations indicated or with 500 µg/ml of the unrelated EVGTGSCNLECVSTNPLSGTEQ(SEQ ID NO:4) control peptide for 2 h. Cells were plated on transwell chambers and allowed to migrate for 20 h in 10% serum-containing medium. Cells that traversed to the undersurface of the filter were stained and the filter area was scanned. The results show mean optical density±S.D. from triplicate wells. The optical density of blank Transwell without cells was of 0.000.

FIG. 6 shows comparison of the efficacy of the MMP inhibitors CTTHWGFTLC(SEQ ID NO:3) and CMT-8 to prevent migration of C8161 melanoma cells. Cells were pretreated with CTTHWGFTLC(SEQ ID NO:3), CMT-8, or with the EVGTGSCNLECVSTNPLSGTEQ(SEQ ID NO:4) control, and allowed to migrate 20 h in Transwell chambers. Cells that migrated to the undersurface of the filter were stained and scanned. The results show mean optical density±S.D. from triplicate wells.

FIG. 7 shows inhibition of endothelial cell migration by CTTHWGFTLC(SEQ ID NO:3). Endothelial cells were allowed to migrate for 18 h in the presence of 20% serum for HUVEC, or 10% serum for Eahy92 line. Shown is the relative number of cells having traversed to the undersurface of Transwell chambers. The results show means±SD from triplicate wells.

FIG. 8 shows inhibition of Matrigel invasion of tumor cells by CTTHWGFTLC(SEQ ID NO:3). C8161 or HT1080 cells were allowed to invade through Matrigel for 24 h in 10% serum-containing medium. The concentrations of CTTHWGFTLC(SEQ ID NO:3) and the EVGTGSCNLECVSTNPLSGTEQ(SEQ ID NO:4) control were 500 μg/ml. The invaded cells were counted, and the relative number of cells are expressed as means±S.D. from triplicate wells.

Figure 1:
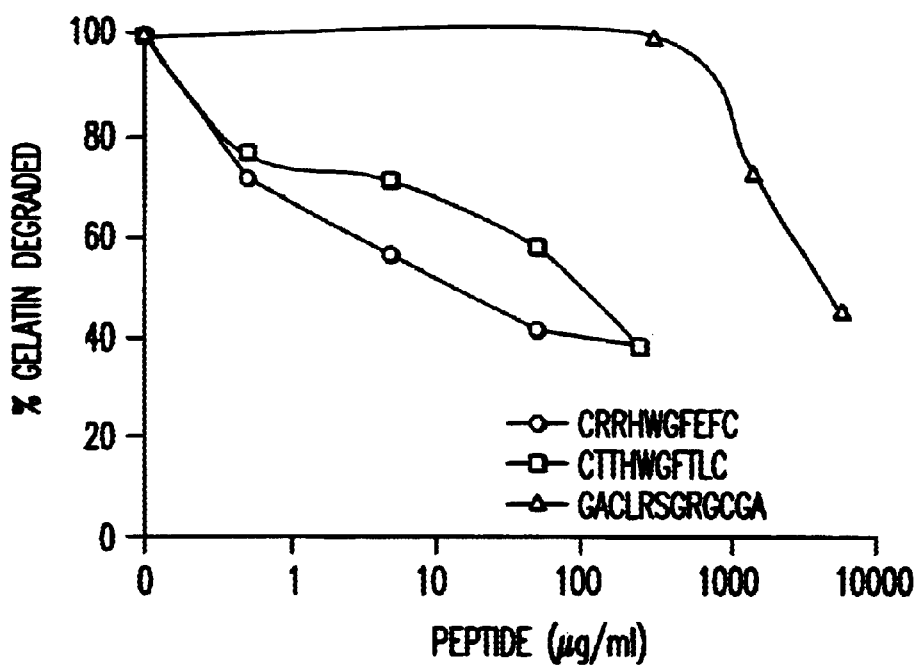

The following examples illustrate the invention without, however, limiting it in any way.

EXAMPLE 1

Preparation of Phage Display Libraries and Selection of MMP-9-binding Phage

The single cysteine-expressing $CX_9$ library was prepared according to the methods described previously (Koivunen et al., 1994a; Koivunen et al., 1994b; and Koivunen et al., 1995, which are all incorporated herein by reference).

ProMMP-9 was purified from human neutrophils and activated with aminophenyl mercuric acetate (APMA) essentially as described by Hibbs et al. (1985). For the selection of MMP-9 binding phage, APMA-activated MMP-9 was coated on microtiter wells overnight at 4° C. using a concentration of 1 μg/ml, after which the cells were saturated with 5 % bovine serum albumin. In the first panning, the library was incubated overnight at 4° C. in 50 mM Tris-HCl/0.1 M NaCl buffer (pH 7.5) (TBS) containing 1% bovine serum albumin, and after extensive washing the bound phage were eluted with low pH buffer. In the subsequent pannings, the amplified phage were allowed to bind for 1 h at 22° C. Randomly selected clones were amplified overnight and sequenced as described by Koivunen et al. (1994b). The binding of each clone to the MMP-9 was verified by attachment assay, in which the cloned phage were incubated for 60 min in MMP-coated or in blank microtiter wells. The wells were washed five times with TBS containing 0.5% Tween 20. The bound phage were quantitated by adding 50 ng per well of anti-M13 antibody (Pharmacia, Uppsala, Sweden) labeled with an Europium-chelate (Wallac Ltd., Turku, Finland). After incubation for 45 min followed by washing, the fluorescence was measured with 1230 Arcus fluorometer (Wallac Ltd., Turku, Finland).

Three MMP-9 binding sequences, CRRHWGFEFC(SEQ ID NO:2), CTTHWGFTLC(SEQ ID NO:3) and CSLHWGFWWC(SEQ ID NO:6), were derived from the $CX_9$ library. All three contained a second cysteine showing a cyclic structure CXXHWGFXXC(SEQ ID NO:1). In spite of several attempts, we could isolate only three HWGF(SEQ ID NO:13)-containing phage apparently because of the dominance of the LRSGRG(SEQ ID NO:7) motif in the selected clones. We therefore constructed a peptide library, where random tetrapeptides (and thus also HWGF(SEQ ID NO:13)) were flanked on both sides by cysteine residues, which could make several disulfide bridges and thereby constrict the peptide conformation. This $CX_3CX_4CX_2C$ (SEQ ID NO:14) library expressed three different peptide ring sizes with two, three and four random residues. On panning with MMP-9, this library yielded the WGF, YGF and FGF motifs, which are similar to the HWGF(SEQ ID NO:13) consensus except that histidine was not conserved.

EXAMPLE 2

Synthesization of Peptides and Determination of Their MMP Inhibitor Activity by Enzyme Inhibition Assays We synthesized cyclic peptides corresponding to those phage motifs of Example 1 that showed the highest avidity for MMP-9, and determined the metalloproteinase inhibitor activity of the synthetic peptides using gelatin and casein degradation assays.

Peptides were synthesized on an Applied Biosystems model 433A (Foster City, Calif.) using Fmoc-chemistry and cyclized in 5% acetic acid (pH 6.0) containing 20% dimethyl sulfoxide overnight at room temperature with constant mixing. After dilution 1:2 with 0.1% trifluoro acetic acid, peptides were purified with reverse-phase HPLC. The structures of the peptides were confirmed by mass spectrometry. Peptides were stored in a stock solution of 100 mg/ml in $H_2O$, and were diluted to buffers with neutral pH just before use.

For the gelatin and casein degradation assays, purified MMP-2 and MMP-9 (50–100 ng) were first incubated for 60 min with various concentrations of the peptide inhibitors, after which a 21 kDa β-casein (52 μM) or $[^{125}I]$-gelatin substrate was added. After incubation for 2 h at 22 ° C., degradation of the casein was analyzed by SDS gel electrophoresis. The degradation of $[^{125}I]$-gelatin was determined by counting radioactivity in the supernatant after precipitation of undegraded gelatin with 20% trichloroacetic acid.

Of a series of peptides synthesized, the HWGF(SEQ ID NO:13) motif-containing peptides CRRHWGFEFC(SEQ ID NO:2) and CTTHWGFTLC(SEQ ID NO:3) were found to be most promising inhibitors of MMP-9. In the $[^{125}I]$-gelatin degradation assay, CRRHWGFEFC(SEQ ID NO:2) was the more active of the two peptides and inhibited APMA-activated MMP-9 with a half-maximal inhibitory value ($IC_{50}$) of about 10 μg/ml (FIG. 1).

Figure 2:
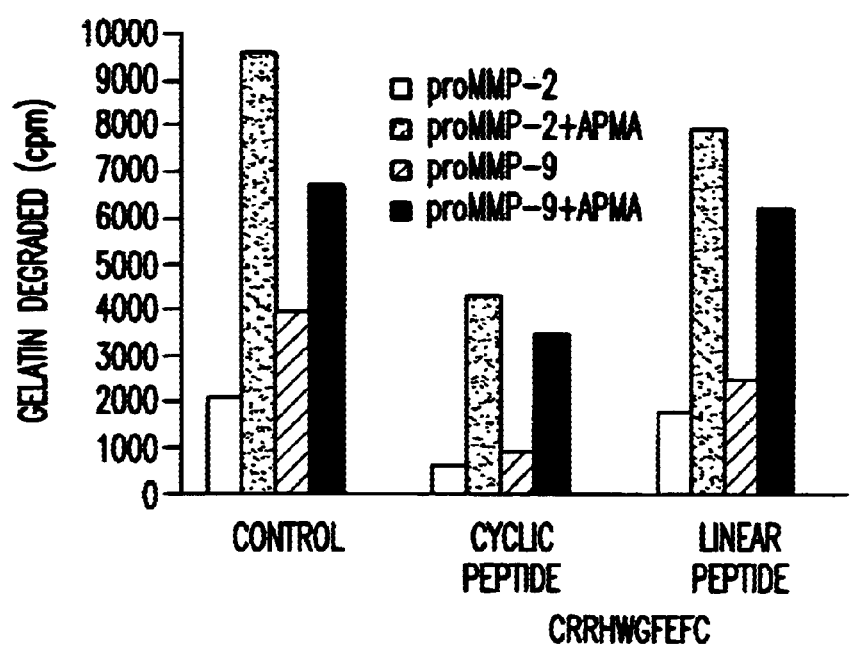

The HWGF(SEQ ID NO:13)-containing peptides also inhibited the gelatinolytic activity mediated by proMMP-9 that autoactivates during incubation with gelatin. FIG. 2 shows that more than 50% inhibition of proMMP-9 activity was obtained with the CRRHWGFEFC(SEQ ID NO:2) peptide at a concentration of 10 μg/ml. To assess the importance of the disulfide bond for the activity of the CRRHWGFEFC(SEQ ID NO:2) peptide, we prepared a linearized version of the peptide by reducing and alkylating the cysteine residues as described by Koivunen et al. (1993). Linearization of the peptide resulted in a loss of inhibitory activity against proMMP-9 as well as the APMA-activated enzyme (FIG. 2).

proMMP-2 was purified from serum-free culture medium of human gingival fibroblasts. The two HWGF(SEQ ID NO:13)-containing peptides CRRHWGFEFC(SEQ ID NO:2) and CTTHWGFTLC(SEQ ID NO:3) also inhibited MMP-2, and at a concentration of 10 μg/ml the cyclic CRRHWGFEFC(SEQ ID NO:2) peptide blocked gelatinolysis by both proMMP-2 and APMA-activated MMP-2 (FIG. 2). The linear peptide used as a control was virtually inactive.

Figure 3:
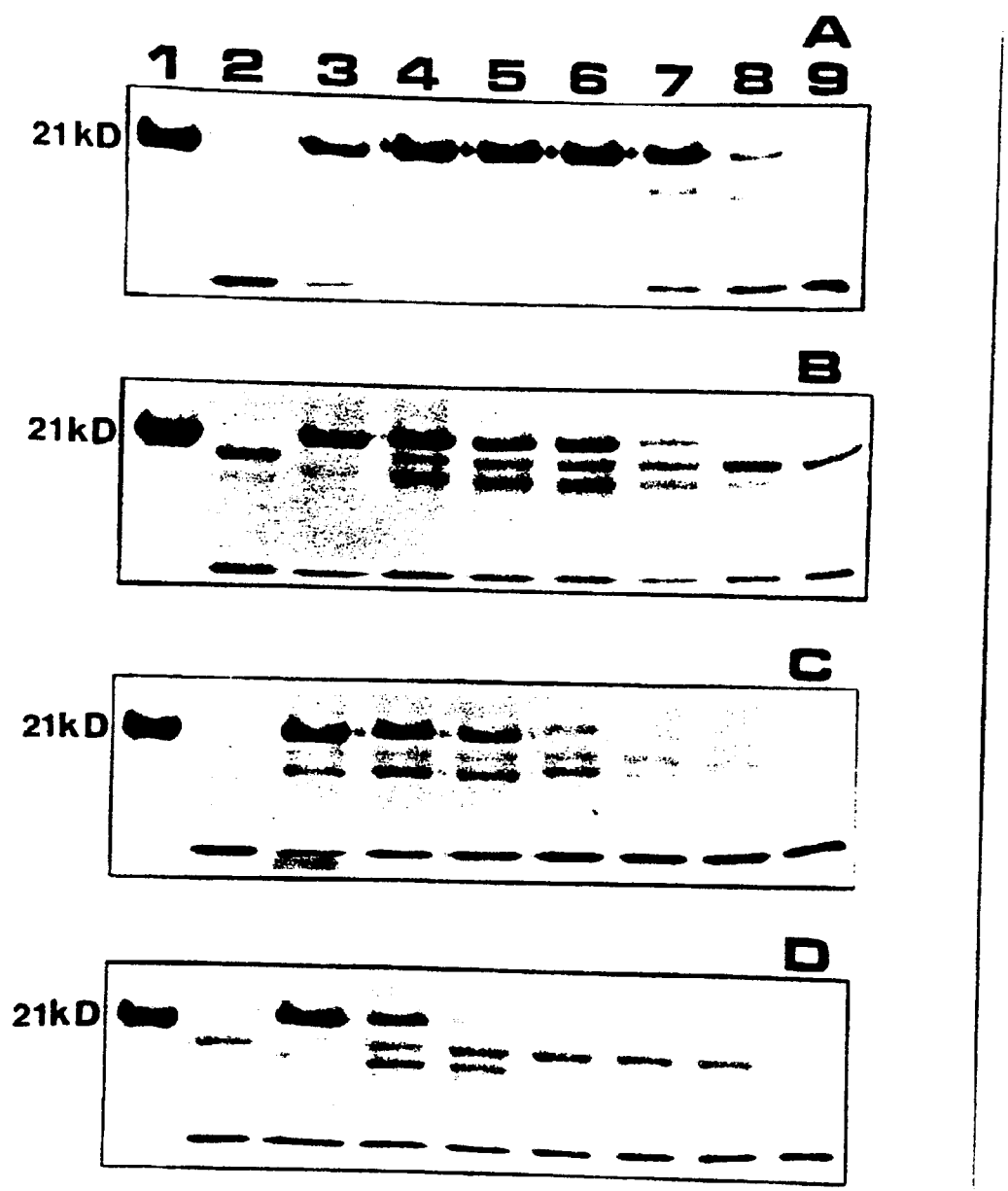

We also used β-casein as a substrate for the gelatinases and analyzed the degradation products by SDS gel electrophoresis. The two HWGF(SEQ ID NO:13)-containing peptides effectively prevented the degradation of casein by the MMPs. For MMP-2, the CTTHWGFTLC(SEQ ID NO:3) and CRRHWGFEFC(SEQ ID NO:2) peptides had $IC_{50}$ values of about 5 µg/ml and 25 µg/ml, respectively (FIGS. 3A and 3C). proMMP-2 not preactivated with APMA also caused casein degradation, and this was blocked by the peptides at the same $IC_{50}$ of 5 µg/ml and 25 µg/ml, respectively (FIGS. 3B and 3D). Caseinolysis by MMP-9 was similarly inhibited by the peptides at low micromolar concentrations except that CRRHWGFEFC(SEQ ID NO:2) was a slightly more potent inhibitor for this MMP than CTTHWGFTLC(SEQ ID NO:3). These peptides (0–200 µ/ml) did not inhibit membrane-type matrix metalloproteinase-1 (MT1-MMP), providing evidence for the importance of gelatinases (MMP-9 and -2) in tumor invastion and basement membrane destruction.

EXAMPLE 3

Extraction of ProMMP-9 by Peptide Affinity Chromatography

To demonstrate that the synthetic peptides selected from the phage libraries recognize MMP-9, we performed affinity chromatography with the peptides coupled to Sepharose.

Affinity chromatography resin of CTTHWGFTLC(SEQ ID NO:3) was prepared by coupling 2 mg peptide per 1 ml of CNBr-activated Sepharose according to the instructions of the manufacturer (Pharmacia, Uppsala, Sweden). Human buffy coat cells obtained from Finnish Red Cross were lysed in 50 mM TBS containing 1% octyl glucoside, and 20 ml of the cleared extract was applied to each peptide Sepharose. The columns were washed until the $OD_{280}$ was below 0.01. The bound proteins were eluted with 0.1 M glycine-HCl buffer, pH 2.2, in the presence of 1% octyl glucoside. The pH was then neutralized with 1 M Tris base. Twenty µl of the fractions were analyzed by SDS gel electrophoresis on 8% acrylamide gels under reducing conditions. Proteins were stained with Coomassie Blue. For immunoblot analysis, nitrocellulose filters were incubated with polyclonal MMP-9 antibodies at a 1:500 dilution for 1 h followed by secondary antirabbit antibodies at a 1:1000 dilution for another 1 h. The enhanced chemiluminescence system (Amersham, Buckinghamshire, England) was used for visualization.

Figure 4:
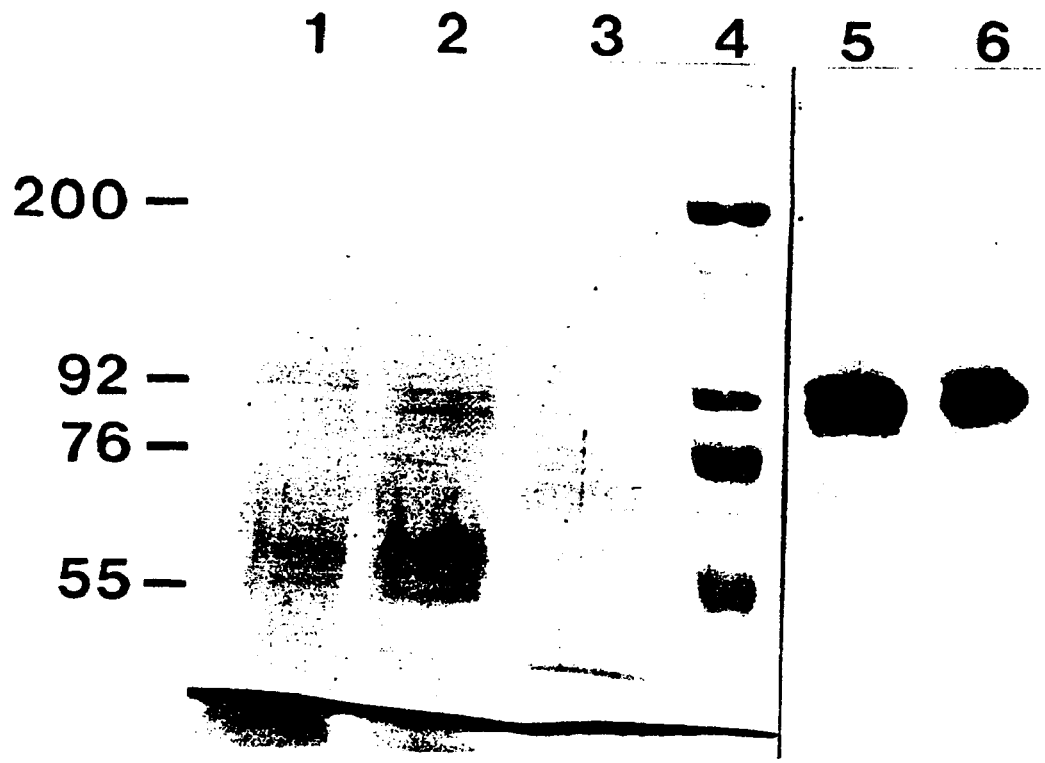

Extracts from leukocytes were applied to Sepharose columns coupled with CTTHWGFTLC(SEQ ID NO:3) and the proteins bound were analyzed by SDS gel electrophoresis and immunoblotting with anti-MMP-9 antibodies. The peptide column bound a set of polypeptides one of which was the 92 kDa proMMP-9 (FIG. 4). ProMMP-9 bound to the CTTHWGFTLC(SEQ ID NO:3) Sepharose migrated on SDS gels as a doublet at 92 kDa (lane 1), both forms of which were immunoreactive with anti-MMP-9 antibodies (lane 6). A similar doublet can be observed in MMP-9 immunoblots of culture medium conditioned by several tumor cell lines (data not shown). The peptide Sepharose also bound a set of polypeptides migrating at 55–65 kDa, the identity of which are not known and were not studied further.

EXAMPLE 4

Inhibition of Cell Migration by CTTHWGFTLC (SEQ ID NO:3)

To test the effectiveness of the novel HWGF(SEQ ID NO:13)-containing MMP inhibitors on cellular migration, we chose to use the CTTHWGFTLC(SEQ ID NO:3) peptide because of its better solubility.

The endothelial cell line HUVEC (human umbilical vein endothelial cells, obtained from the ATCC, Rockville, Md.) was grown in RPMI 1640 medium containing penicillin (100 units/ml), streptomycin (100 µg/ml), 10 mM HEPES, 30 µg/ml endothelial cell growth supplement (Biomedical Technologies, Stoughton, Mass.), and 20% fetal calf serum. The HT1080 fibrosarcoma cells (ATCC, Rockville, Md.), C8161 melanoma cells and Eahy926 cells (derivative of HUVEC) were cultured in Dulbecco's modified Eagle's medium containing the antibiotics, 10% fetal calf serum, and hypoxanthine/aminopterin/thymidine additive with the Eahy926 cells. Cultures of cells were harvested with trypsin-EDTA (endothelial cells) or EDTA alone (other cells), washed, and resuspended in the full serum-containing media as indicated above.

Random cell migration was studied using 8.0 µM pore size and 6.5 mm diameter Transwell inserts (Costar, Cambridge, Mass.) that were equilibrated in the serum-containing medium for 2 h before use. Tumor cell invasion was studied using 6.4 mm diameter Boyden chambers precoated with Matrigel (Becton Dickinson, Bedford, MA) and equilibrated in the serum-containing medium. 750 µl of the serum containing media were added to the lower compartments of the migration apparatus. For random migration assays, cells were preincubated for 2 h in the presence of the peptides at the concentration indicated, and 20 000 cells in a volume of 100 µl were plated in a Transwell. For Matrigel invasion, each well was plated with 100 000 cells in a 500 µl volume with or without the peptides. After culturing cells for 16–20 h, cells were fixed in methanol, washed, and stained in toluidine blue. Cells were removed from the upper surface of the membrane with a cotton swab, and the cells migrated on the undersite of the membrane were counted microscopically, or alternatively quantitated by scanning.

Figure 5:
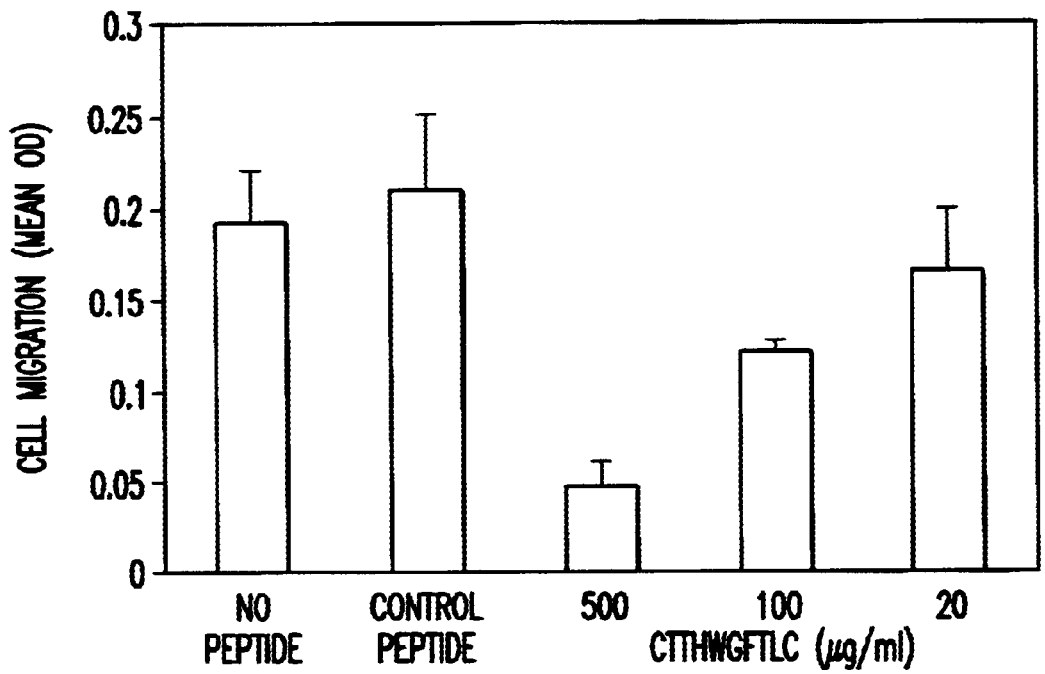

The CTTHWGFTLC(SEQ ID NO:3) peptide was capable of blocking migration of a variety of cell lines studied in the presence of 10 or 20% serum. In the Transwell random migration assay, the peptide inhibited concentration-dependently the motility of HT1080 fibrosarcoma cells (FIG. 5). At the concentrations of 500 and 100 µg/ml, the peptide inhibited by 80 and 40%, respectively. For the purpose of control, we synthesized a scrambled CWLTFTHGTC(SEQ ID NO:8) but could not use it because of its lack of solubility in aqueous buffers. We therefore used three unrelated highly soluble peptides EVGTGSCNLECVSTNPLSGTEQ(SEQ ID NO:4), CQWNNDNPLFKEAEEEVMNPKFAES(SEQ ID NO:9), and RAVRALWRC(SEQ ID NO:10). None of these control peptides affected cell migration at a concentration of 500 µg/ml (FIG. 5, and data not shown). CTTHWGFTLC(SEQ ID NO:3) was not found to block cell surface integrins as the peptide did not prevent initial attachment and spreading of cells on fibronectin, collagen IV, or Matrigel substrata. No significant decrease in cell viability was noted after one or two-day culture of cells in the presence of the peptide (data not shown).

Figure 6:
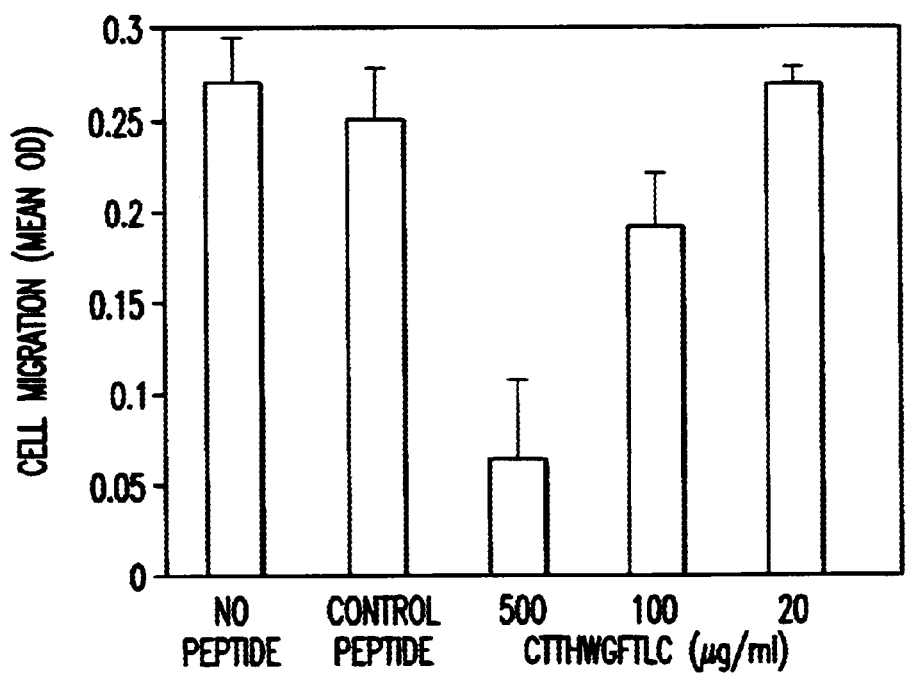

CTTHWGFTLC(SEQ ID NO:3) similarly inhibited random migration of C8161 melanoma cells, maximally by 80% at the concentration of 500 µg/ml (FIG. 6). The three control peptides did not affect cell migration.

Figure 7:
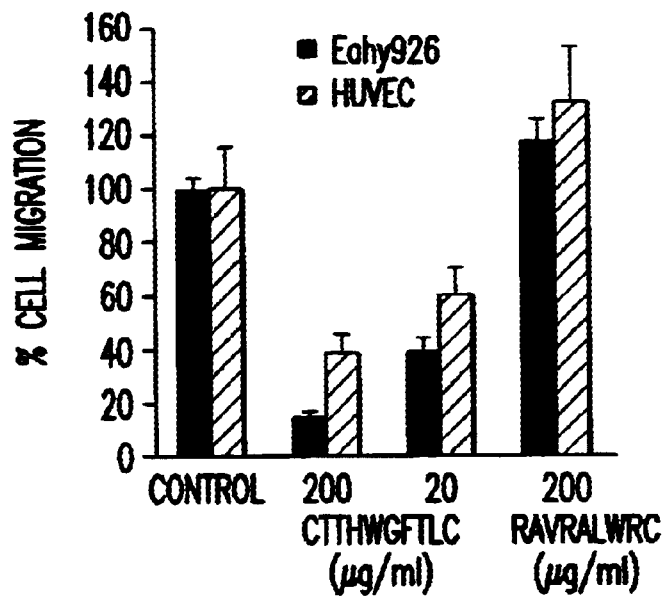

We also studied the effect of CTTHWGFTLC(SEQ ID NO:3) on the random migration of endothelial cells in the Transwell assay (FIG. 7). At a concentration of 200 µg/ml, the peptide showed 85 and 60% inhibition of migration of Eahy 926 and HUVEC cells, respectively, and was still capable to partially inhibit at a concentration of 20 μg/ml. The RAVRALWRC(SEQ ID NO:10) peptide did not cell block cell migration.

Figure 8:
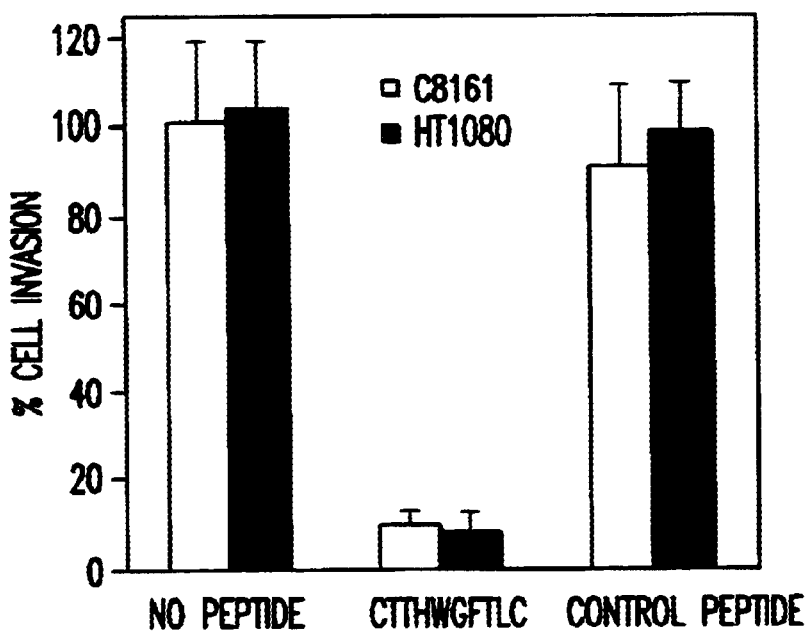

Finally, we examined the ability of CTTHWGFTLC(SEQ ID NO:3) to prevent Matrigel invastion of HT1080 and C8161 cells. In both cell lines, the peptide strongly suppressed invasion, and the inhibition was maximally 90% at 500 μg/ml, the highest concentration studied (FIG. 8). None of the three control peptides affected Matrigel invasion.

EXAMPLE 5

Suppression of Growth of Human Breast Carcinoma Xenografts in Athymic Mice by Locally Applied CTTHWGFTLC(SEQ ID NO:3)

Figure 9:
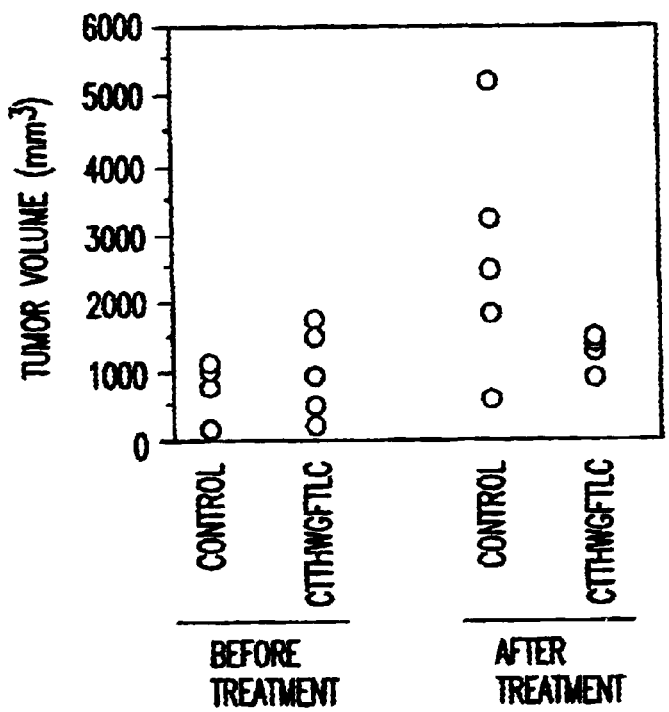
FIG. 9 shows that breast carcinoma growth is clearly inhibited by CTTHWGFTLC(SEQ ID NO:3) peptide.

Mice bearing human breast carcinomas were developed by inoculating $1 \times 10^6$ MDA-B-435 cells in the fat mammary pad. After 4 weeks the volumes of the tumors were calculated by measuring the diameters in the three dimensions. The mice were divided in two groups each consisting of five animals. One group was treated with 200 μg of CTTHWGFTLC(SEQ ID NO:3) in a 200 μl volume administered three times a week adjacent to the tumor. The second group was given the cyclic peptide control CVRNSLAC (SEQ ID NO:11). The tumor volumes were measured weekly; the results are after three-week treatment with the peptide (FIG. 9). The results show that CTTHWGFTLC (SEQ ID NO:3) peptide clearly inhibits breast carcinoma growth.

EXAMPLE 6

Figure 10:
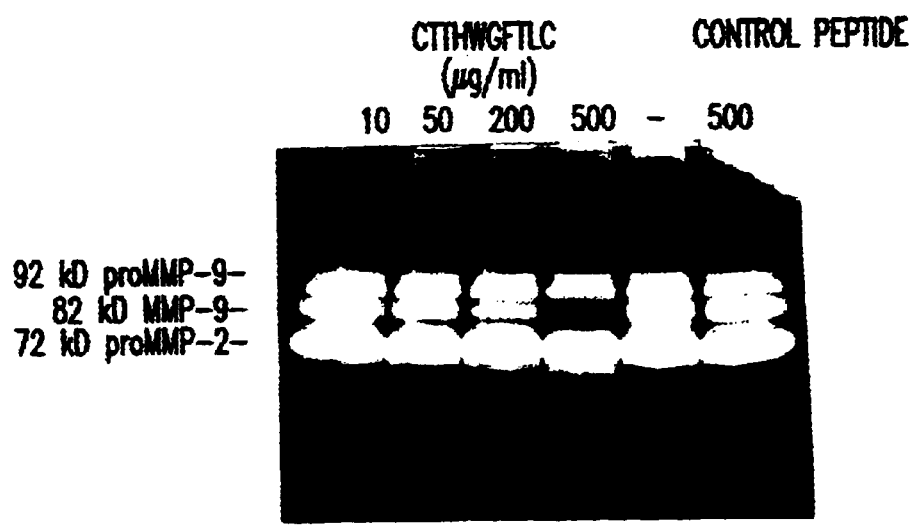
FIG. 10 shows gelatin zymography of melanoma cell conditioned medium. CTTHWGFTLC(SEQ ID NO:3) peptide but not the control peptide inhibits the formation of active 82 kD MMP-9.

Deactivation of ProMMP-9 by CTTHWGFTLC (SEQ ID NO:3) as Detected by Gelatin Zymography C8161 melanoma cells were cultivated for 48 h in 24-well plates in medium containing 10% serum. The CTTHWGFTLC(SEQ ID NO:3) peptide was included at the concentrations indicated in FIG. 10 (500–10 μg/ml) and the control peptide RAVRALWRC(SEQ ID NO:10) at 500 μg/ml. The conditioned medium was analyzed by SDS gel electrophoresis followed by gelatin zymography. CTTHWGFTLC(SEQ ID NO:3) decreased concentration-dependently the levels of 82 kDa active MMP-9, but did not affect the levels of 72 kDa proMMP-2.

EXAMPLE 7

Figure 11A:
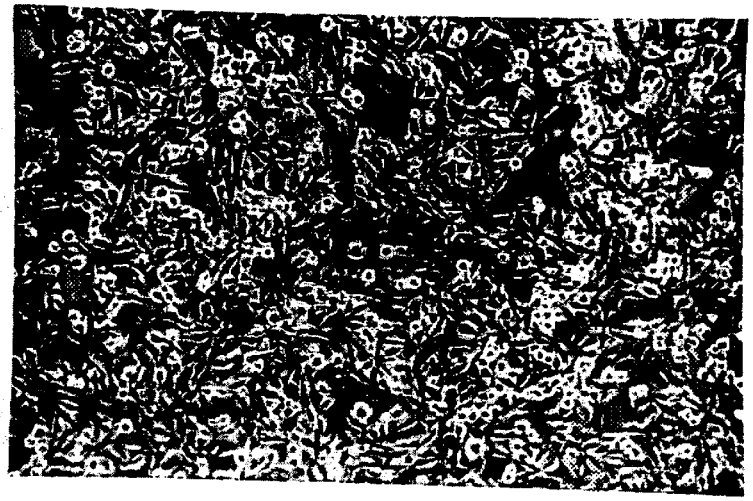
FIGS. 11A, 11B and 11C show MB-435 breast carcinoma cells grown for 2 days in 10% serum in the absence or presence of CTTHWGFTLC(SEQ ID NO:3) peptide.
Figure 11B:
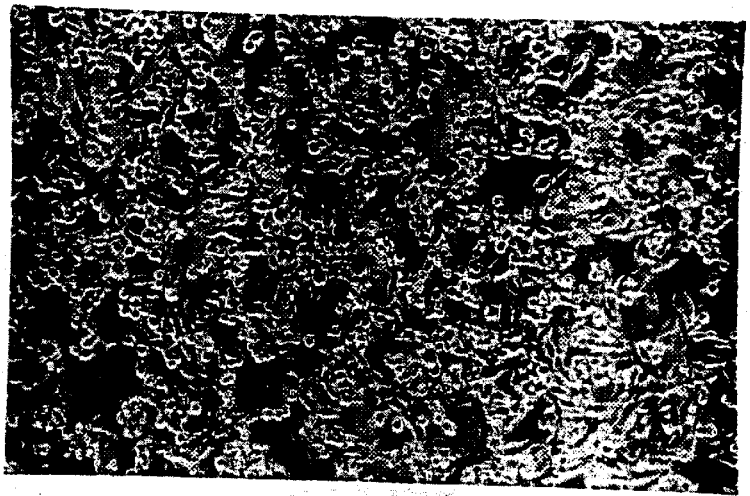
Figure 11C:
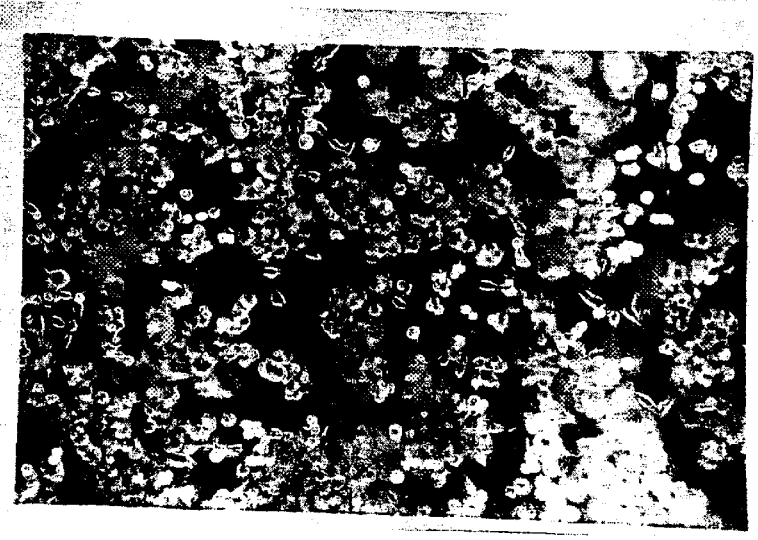

Time-dependent Induction of Rounded Cell Morphology and Detachment of the Cells From the Substratum MB-435 breast carcinoma cells were cultivated for 48 h in 10% serum-containing medium in the absence or presence of the CTTHWGFTLC(SEQ ID NO:3) peptide, after which cells were analyzed by light microscope. Unrelated synthetic peptides studied at the same concentrations had no effect on the morphology of cell layers. Rounded cell morphology is detectable within 16–24 h after applying CTTHWGFTLC (SEQ ID NO:3) but is not evident in short-time culture (FIGS. 11A to 11C); the peptide had no effect on the initial attachment of cells on the substratum during 1 or 2 h time scale.

EXAMPLE 8

Effect of CTTHWGFTLC(SEQ ID NO:3) on Cell Viability

To assess the effect of CTTHWGFTLC(SEQ ID NO:3) on cell viability, 100 000 cells were plated in 24-well plates in 1 ml of medium containing 10% fetal calf serum and 500 μg/ml of CTTHWGFTLC(SEQ ID NO:3) or an unrelated control peptide. After culturing for 20 or 40 h, the viability was determined by staining with trypan blue, or with the MTT reagent according to the instructions of the manufacturer (Sigma, St. Louis). For cell adhesion studies, microtiter wells were coated with fibronectin (Finnish Red Cross), type IV collagen (Sigma) or Matrigel, and blocked with BSA. Cells (100 000 cells per well) were incubated together with 500 μg/ml of CTTHWGFTLC(SEQ ID NO:3) or a control peptide in a serum-free medium for 1 h. After washing twice with PBS, the bound cells were stained and counted.

The peptide was not found to affect cell number or viability by trypan blue dye exclusion, and has shown no toxicity when injected into animals. The peptide did not prevent initial attachment of cells on Matrigel, collagen or fibronectin.

EXAMPLE 9

Figure 12:
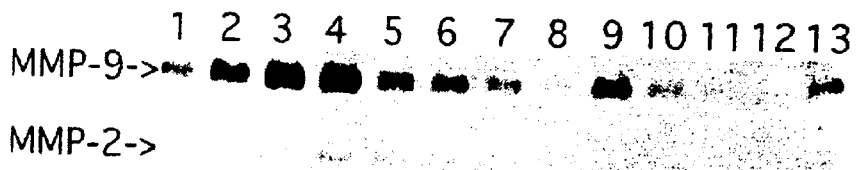
FIG. 12 shows the effect of CTTHWGFTLC(SEQ ID NO:3) (P291) on keratinocyte gelatinase production and expression.

Effect of CTTHWGFTLC(SEQ ID NO:3) on Keratinocyte Gelatinase Production and Expression 30 000 HaCat cells (spontaneously transformed non-tumorigenic human keratinocyte cell line, Ryle el al., 1989) were seeded into the wells of 96-well plates (Nunclon, Denmark) in 50 μl of KGM and allowed to attach for 24 h in humidified atmosphere at 37° C. Then the cells were exposed to KGM or KGM containing 50–500 μg/ml of CTTHWGFTLC(SEQ ID NO:3) with or without 10 μg/ml of TGFβ. A set of cultures were treated with 1, 10 or 20 ng/ml of TGFβ alone. After 24 h the medium was harvested and stored at −20° C. until analyzed by zymography (Heussen & Dowdle, 1980). 12 μl of the culture media were run in 10% SDS-polyacrylamide gels containing 1.0 mg/ml 2-methoxy-2,4-diphenyl-3(2H)-furanone-labelled gelatin (O'Grady et al.; 1984). The lysis of gelatin was monitored by long wave UV-light and the gels were photographed. A computerized densitometer (MCID-M4, Imaging research Inc., St. Catherines, Ontario, Canada) was used to measure the amount of gelatinases from the photographed gels. The cells in the plates were fixed with 4% (v/v) formaldehyde in PBS containing 5% (v/v) sucrose, and stained with 0.1% crystal violet in boric acid (pH 6.0) for 20 min. After destaining with 10% acetic acid, the absorbancies were measured with Multiscan MS plate reader (Version 4.0, Labsystems, Helsinki, Finland) at 595 nm. The relative cell number obtained by this method was used when the amount of gelatinases per cell was counted. Only MMP-9 gave measurable cleavage rate in order to calculate the amount of the enzyme per cell. The results shown in FIG. 12 are mean of two experiments.

EXAMPLE 10

Figure 13:
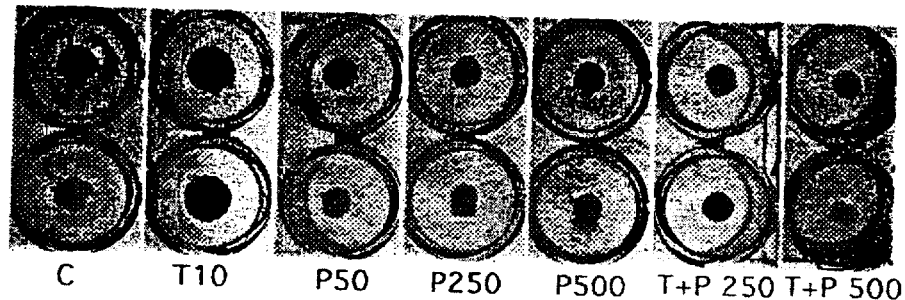
FIG. 13 shows the effect of CTTHWGFTLC(SEQ ID NO:3) (P291) on keratinocyte migration. The photograph of the plates is taken after 4 days of migration.

Effect of CTTHWGFTLC(SEQ ID NO:3) on Keratinocyte Migration 24-well plates (Costar, Cambridge, Mass., USA) were coated with 50 μg/ml of fibronectin (FN; from human plasma; Sigma, F-2006, St. Louis, Mo., USA) in PBS (pH 7.4). Metal cylinders were placed into the coated wells and 50 000 Ha-Cat cells in KGM media (in 50 μl) were seeded into the cylinders. The cells were allowed to attach to the substrate for 24 h at 37° C. in humidified atmosphere. The cylinders were removed, and the non adherent cells were removed by washing with the culture medium, the medium was replaced with KGM containing various concentrations of CTTHWGFTLC(SEQ ID NO:3) or TGFβ. Cells were allowed to migrate out from the disk for 4 days at 37° C. The medium was harvested and cells were fixed with 4% (v/v)

formaldehyde in PBS containing 5% (v/v). sucrose, and stained with 0.1% crystal violet in boric acid (pH 6.0). The wells were photographed and the amount of migration was measured by counting the area of migrated cells using NIH Image 1.45 program for Macintosh computer. A photograph of the plates after 4 days of migration and calculated areas of migrated cells are shown in FIG. 13. The results are mean of two duplicate experiments.

Sequence Listing Free Text

For Seq. ID No. 1:

Variable aa, Xaa in position 2 can be any amino acid

Variable aa, Xaa in position 3 can be any amino acid

Variable aa, Xaa in position 8 can be any amino acid

Variable aa, Xaa in position 9 can be any amino acid

References

Arap, V., Pesquelini, R., Ruoslahti, E. (1998), Cancer treatment by targeted drug delivery to tumor vasculature in a mouse model, Science 279, 377–379.

Beckett, R. P., Davidson, A. H., Drummond, A. H., Huxley, P. & Whittaker, M. (1996), Recent advances in matrix metalloproteinase inhibitor research, Drug Design Today, 1, 16–26.

Birkendal-Hansen, H. et al. (1993), Matrix metalloproteinases: a review, Crit. Rev. Oral Biol. Med. 4:197–250.

Birkendal-Hansen, H. (1995), Proteolytic remodeling of extracellular matrix, Curr. Opin. Cell Biol. 7, 728–735.

Chandler, S., Miller, K. M., Clements, J. M., Lury, J., Corkill, D., Anthony, D. C. C., Adams, S. E., Gezviny, A. J. H. (1997), Matrix metalloproteinases, tumor necrosis factor and multiple sclerosis: an overview, J. Neuroimmunol. 72, 155–161.

Dennis, M., Herzka, A. & Lazarus, R. A. (1995), Potent and selective Kunitz domain inhibitors of plasma kallikrein designed by phage display, J. Biol. Chem. 270, 25411–25417.

Fotouhi, N., Lugo, A., Visnick, M., Lusch, L., Walsky, R., Coffey, J. W. & Hanglow, A. C. (1994), Potent peptide inhibitors of stromelysin based on the prodomain region of matrix metalloproteinases, J. Biol. Chem. 269, 30227–30231.

Golub, L. M., Suomalainen, K., Sorsa, T. (1992), Host modulation by tetracyclines and their chemically modified derivatives, Curr. Op. Dent. 2, 80–90.

Hanahan, D. & Folkman, J. (1996), Patterns and emerging mechanisms of the angiogenic switch during tumorigenesis, Cell 86, 353–364.

Heussen, C. & Dowdle, E. B. (1980), Electrophoretic analysis of plasminogen activators in polyacrylamide gels containing sodium dodecyl sulfate and copolymerized substrates, Anal. Biochem. 102, 196–202.

Hibbs, M. S., Hasty, K. A., Seyer, J. M., Kang, A.H. & Mainardi, C. L. (1985) J. Biol. Chem. 260, 2493–2500.

Koivunen, E., Gay, D. A. & Ruoslahti, E. (1993), Selection of peptides binding to the $\alpha_5\beta_1$ integrin from phage display library, J. Biol. Chem. 270, 20205–20210.

Koivunen, E., Wang, B. & Ruoslahti, E. (1994a) J. Cell Biol. 124, 373–380.

Koivunen, E., Wang, B., Dickinson, G. D. & Ruoslahti, E. (1994b) Methods Enzymol. 245, 346–369.

Koivunen, E., Wang, B. & Ruoslahti, E. (1995), Phage libraries displaying cyclic peptides with different ring sizes: ligand specificities of the RGD-directed integrins, Bio/Technology 13, 265–270.

Krane, S. M. (1994), Clinical importance of matrix metalloproteinases and their inhibitors, Ann. N. Y. Acad. Sci. 732, 1–10.

Llano, E., Pendus, A. M., Knanper, V., Sorsa, T., Salo, T., Salido, E., Murphy, G., Simmer, J. P., Bartlett, J., Lopez-Otin, C. (1997), Identification and structural characterization of human enamelysin MMP-20, Biochemistry 36, 15101–15108.

Matthews, D. J. & Wells, J. A. (1993), Substrate phage: selection of protease substrates by monovalent phage display, Science, 260, 1113–1117.

Melchiori, A., Albini, A., Ray, J. M. & Stetler-Stevenson, W. G. (1992), Inhibition of tumor cell invasion by a highly conserved peptide sequence from the matrix metalloproteinase enzyme prosegment, Cancer Res. 53, 2353–2356.

O'Grady, R. L., Nethery, A., Hunter, N. (1984), A fluorescent screening assay for collagenase using collagen labelled with 2-methoxy-2,4-diphenyl-3(2H)-furanone, Anal. Biochem. 140, 490–494.

Park, A. J., Matrisian, L. M., Kells, A. F., Pearson, R., Yuan, Z. & Navre, M. (1991), Mutational analysis of the transin (rat stromelysin) autoinhibitor region demonstrates a role for residues surrounding the "cysteine switch", J. Biol. Chem. 266, 1584–1590.

Pei, D., Weiss, (1996) J. Biol. Chem. 271, 9135–9140.

Roberts, B. L., Markland, W., Ley, A. C., Kent, R. B., White, D. W., Guterman, S. K. & Ladner, R. C. (1992), Directed evolution of a protein: selection of potent neutrophil elastase inhibitors displayed on M13 fusion phage, Proc. Natl. Acad. Sci. USA, 89, 2429–2433.

Ryle, C. M., Breitkreutz, D., Stark, H-J., Leigh, I. M., Steinert, P. M., Roop, D., Fusenig, N. E. (1989), Density-dependent modulation of synthesis of keratins 1 and 10 in human keratinocyte line HaCat and in ras-transfected tumorigenic clones, Differentiation, 40, 42–54.

Shapira, L., Houri, Y., Barak, V., Soskolne, W. E., Halabi, A., Stahholz (1997), Tetracycline inhibits Porphyromones gingivalis—induced lesion in vivo and TNF-processing in vitro, J. Periodont. Res. 32, 183–185.

Smith, M. W., Shi, L. & Navre, M. (1995), Rapid identification of highly active and selective substrates for stromelysin and matrilysin using bacteriophage peptide display libraries, J. Biol. Chem. 270, 6440–6449.

Sorsa, T., Ding, Y., Salo, T., Lauhio, A., Teronen, O., Ingman, T., Ohtani, H., Andoh, N., Takeha, S. & Konttinen, Y. T. (1994), Effects of tetracyclines on neutrophil, gingival, and salivary collagenases. A functional and western-blot assessment with special reference to their cellular sources in periodontal diseases, Ann. N. Y. Acad. Sci. 732, 112–131.

Stetler-Stevenson, W. G., Aznavoorian, S. & Liotta, L. A. (1993), Tumor cell interactions with the extracellular matrix during invasion and metastasis, Annu. Rev. Cell Biol. 9, 541–573.

Tryggvason, K., Höyhtyä, M. & Salo, T. (1987), Proteolytic degradation of extracellular matrix in tumor invasion, Biochim. Biophys. Acta 907, 191–217.

Volpert, O. V., Ward, W. F., Lingen, M. W., Chesler, L., Solt, D. B., Johnson, M. D., Molteni, A., Polverini, P. J. & Bouck, N. P. (1996), Captopril inhibits angiogenesis and slows the growth of experimental tumors in rat, J. Clin. Invest. 98, 671–679.

Woessner, J. (1991), Matrix metalloproteinases and their inhibitors in connective tissue remodeling, Faseb J. 5, 2145–2154.

What is claimed is:

1. A matrix metalloproteinase inhibitor and down-regulator comprising the cyclic structure of the peptide motif (SEQ ID NO:1)

Cys-Xaa-Xaa-His-Trp-Gly-Phe-Xaa-Xaa-Cys

Wherein Xaa at position 2 is Arg or Thr, Xaa at position 3 is Arg or Thr, Xaa at position 8 is Glu or Thr, and Xaa at position 9 is Phe or Leu.

2. A matrix metalloproteinase inhibitor and down-regulator comprising the cyclic structure of the peptide motif (SEQ ID NO:2)

Cys-Arg-Arg-His-Trp-Gly-Phe-Glu-Phe-Cys.

3. A matrix metalloproteinase inhibitor and down-regulator comprising the cyclic structure of the peptide motif (SEQ ID NO:3)

Cys-Thr-Thr-His-Trp-Gly-Phe-Thr-Leu-Cys.

4. A composition comprising a matrix metalloproteinase inhibitor and down regulator according to any one of claims 1 to 3 and a pharmaceutically acceptable carrier.

5. A method of inhibiting a matrix metalloproteinase (MMP) selected from the group consisting of MMP-2 and MMP-9 in mammals, comprising administering to said mammal a matrix metalloproteinase inhibitor and down-regulator according to any one of claims 1 to 3 in an amount effective to inhibit MMP-2, MMP-9, or MMP-2 and MMP-9.

6. A process for the preparation of a matrix metalloproteinase inhibit or according to claim 1, comprising the steps of:

synthesizing said matrix metalloproteinase inhibitor via the technique of solid-phase Merrifield peptide synthesis, cyclizing the inhibitor, and isolating the inhibitor.

* * * * *

SEQUENCE LISTING

<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: Targeted to Homo sapiens
<221> NAME/KEY: misc_feature
<222> LOCATION: (2)..(2)
<223> OTHER INFORMATION: Xaa can be any amino acid
<221> NAME/KEY: misc_feature
<222> LOCATION: (3)..(3)
<223> OTHER INFORMATION: Xaa can be any amino acid
<221> NAME/KEY: misc_feature
<222> LOCATION: (8)..(8)
<223> OTHER INFORMATION: Xaa can be any amino acid
<221> NAME/KEY: misc_feature
<222> LOCATION: (9)..(9)
<223> OTHER INFORMATION: Xaa can be any amino acid

<400> SEQUENCE: 1

Cys Xaa Xaa His Trp Gly Phe Xaa Xaa Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Targeted to Homo sapiens

<400> SEQUENCE: 2

Cys Arg Arg His Trp Gly Phe Glu Phe Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Targeted to Homo sapiens

<400> SEQUENCE: 3

Cys Thr Thr His Trp Gly Phe Thr Leu Cys
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Targeted to Homo sapiens

<400> SEQUENCE: 4

Glu Val Gly Thr Gly Ser Cys Asn Leu Glu Cys Val Ser Thr Asn Pro
1               5                   10                  15

Leu Ser Gly Thr Glu Gln
            20

<210> SEQ ID NO 5
<211> LENGTH: 12
<212> TYPE: PRT
<213> ORGANISM: Artificial Sequence
<220> FEATURE:
<223> OTHER INFORMATION: Targeted to Homo sapiens

```
<400> SEQUENCE: 5

Gly Ala Cys Leu Arg Ser Gly Arg Gly Cys Gly Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Targeted to Homo sapiens

<400> SEQUENCE: 6

Cys Ser Leu His Trp Gly Phe Trp Trp Cys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Targeted to Homo sapiens

<400> SEQUENCE: 7

Leu Arg Ser Gly Arg Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Targeted to Homo sapiens

<400> SEQUENCE: 8

Cys Trp Leu Thr Phe Thr His Gly Thr Cys
1               5                   10

<210> SEQ ID NO 9
<211> LENGTH: 25
<212> TYPE: PRT
<213> ORGANISM: Artificial Sequence
<220> FEATURE:
<223> OTHER INFORMATION: Targeted to Homo sapiens

<400> SEQUENCE: 9

Cys Gln Trp Asn Asn Asp Asn Pro Leu Phe Lys Glu Ala Glu Glu
1               5                   10                  15

Val Met Asn Pro Lys Phe Ala Glu Ser
            20                  25

<210> SEQ ID NO 10
<211> LENGTH: 9
<212> TYPE: PRT
<213> ORGANISM: Artificial Sequence
<220> FEATURE:
<223> OTHER INFORMATION: Targeted to Homo sapiens

<400> SEQUENCE: 10

Arg Ala Val Arg Ala Leu Trp Arg Cys
1               5

<210> SEQ ID NO 11
<211> LENGTH: 8
<212> TYPE: PRT
<213> ORGANISM: Artificial Sequence
<220> FEATURE:
```

```
<223> OTHER INFORMATION: Targeted to Homo sapiens

<400> SEQUENCE: 11

Cys Val Arg Asn Ser Leu Ala Cys
1               5

<210> SEQ ID NO 12
<211> LENGTH: 7
<212> TYPE: PRT
<213> ORGANISM: Artificial Sequence
<220> FEATURE:
<223> OTHER INFORMATION: derived from Homo sapiens
<221> NAME/KEY: misc_feature
<222> LOCATION: (5)..(5)
<223> OTHER INFORMATION: Xaa can be any amino acid

<400> SEQUENCE: 12

Pro Arg Cys Gly Xaa Pro Asp
1               5

<210> SEQ ID NO 13
<211> LENGTH: 4
<212> TYPE: PRT
<213> ORGANISM: Artificial Sequence
<220> FEATURE:
<223> OTHER INFORMATION: Derived from Homo sapiens

<400> SEQUENCE: 13

His Trp Gly Phe
1

<210> SEQ ID NO 14
<211> LENGTH: 13
<212> TYPE: PRT
<213> ORGANISM: Artificial Sequence
<220> FEATURE:
<223> OTHER INFORMATION: Targeted to Mammals
<221> NAME/KEY: misc_feature
<222> LOCATION: (1)..(13)
<223> OTHER INFORMATION: Xaa is any amino acid

<400> SEQUENCE: 14

Cys Xaa Xaa Xaa Cys Xaa Xaa Xaa Xaa Cys Xaa Xaa Cys
1               5                   10
```